(12) United States Patent
Desantis et al.

(10) Patent No.: US 6,350,908 B1
(45) Date of Patent: Feb. 26, 2002

(54) PROCESS FOR THE PREPARATION OF S-N, N'-BIS [2-HYDROXY-1-(HYDROXYMETHYL) ETHYL]-5- [(2-HYDROXY-1-OXOPROPYL) AMINO]-2,4,6-TRIIODO-1,3-BENZENEDICARBOXAMIDE

(75) Inventors: Nicola Desantis; Ilaria Peretto, both of Milan (IT)

(73) Assignee: Bracco Imaging S.p.A, Milan (IT)

( * ) Notice: Subject to any disclaimer, the term of this patent is extended or adjusted under 35 U.S.C. 154(b) by 0 days.

(21) Appl. No.: 09/786,884

(22) PCT Filed: Aug. 6, 1999

(86) PCT No.: PCT/EP99/05686

§ 371 Date: Mar. 28, 2001

§ 102(e) Date: Mar. 28, 2001

(87) PCT Pub. No.: WO00/15602

PCT Pub. Date: Mar. 23, 2000

(30) Foreign Application Priority Data

Sep. 11, 1998 (IT) .......................... MI98A1996

(51) Int. Cl.$^7$ ...................... C07C 231/00; C07C 233/00
(52) U.S. Cl. ...................... 564/142; 564/153; 564/155; 564/158
(58) Field of Search ................................. 564/142, 153, 564/155, 158

(56) References Cited

FOREIGN PATENT DOCUMENTS

| GB | 2 272 218 | 5/1994 |
|----|-----------|--------|
| GB | 2 311 524 | 10/1997 |
| WO | WO97/47590 | 12/1997 |

*Primary Examiner*—Samuel Barts
*Assistant Examiner*—Elvis O. Price
(74) *Attorney, Agent, or Firm*—Nixon & Vanderhye

(57) ABSTRACT

A process for the preparation of S-N,N'-bis[2-hydroxy-1-(hydroxymethyl)ethyl]-5-[(2-hydroxy-1-oxopropyl)amino]-2,4,6-triiodo-1,3-benzenedicarboxamide, comprising the reaction of S-(−)-5-[[2-(acetyloxy)-1-oxopropyl]amino]-2,4,6-triiodo-1,3-benzenedicarboxylic acid dichloride (III) with 2-amino-1,3-propanediol (serinol) without a solvent, followed by hydrolysis of the acetate group.

7 Claims, No Drawings

PROCESS FOR THE PREPARATION OF S-N,N'-BIS [2-HYDROXY-1-(HYDROXYMETHYL) ETHYL]-5- [(2-HYDROXY-1-OXOPROPYL) AMINO]-2,4,6-TRIIODO-1,3-BENZENEDICARBOXAMIDE

This is the National phase application of PCT/EP9905686, filed Aug. 6, 1999.

The present invention relates to a process for the preparation of S-N,N'-bis[2-hydroxy-1-(hydroxymethyl)-ethyl]-5-[(2-hydroxy-1-oxopropyl)-amino]-2,4,6-triiodo-1,3-benzenedicarboxamide of formula (I), more commonly known as Iopamidol, which is one of the world top compounds in the field of iodinated contrast agents, which process comprises a novel step for the synthesis of the intermediate S-N,N'-bis[2-hydroxy-1-(hydroxymethyl)ethyl]-5-[(2-(acetyloxy)-1-oxopropyl)-amino]-2,4,6-triiodo-1,3-benzenedicarboxamide of formula (II).

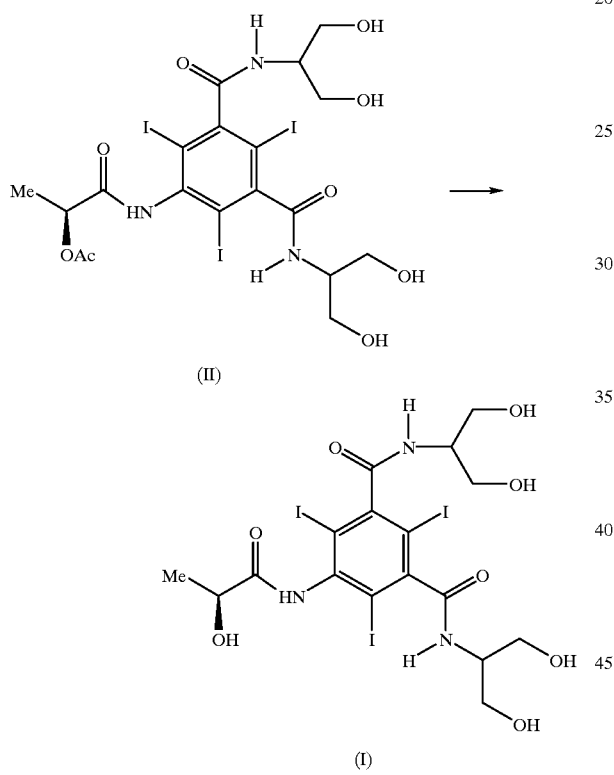

The synthesis of Iopamidol was described first in GB 1.472.050 and it involves the steps represented in the following Scheme:

Scheme

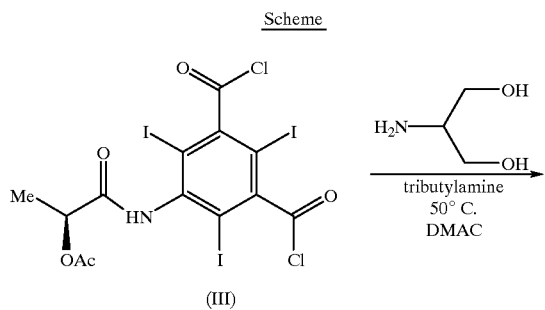

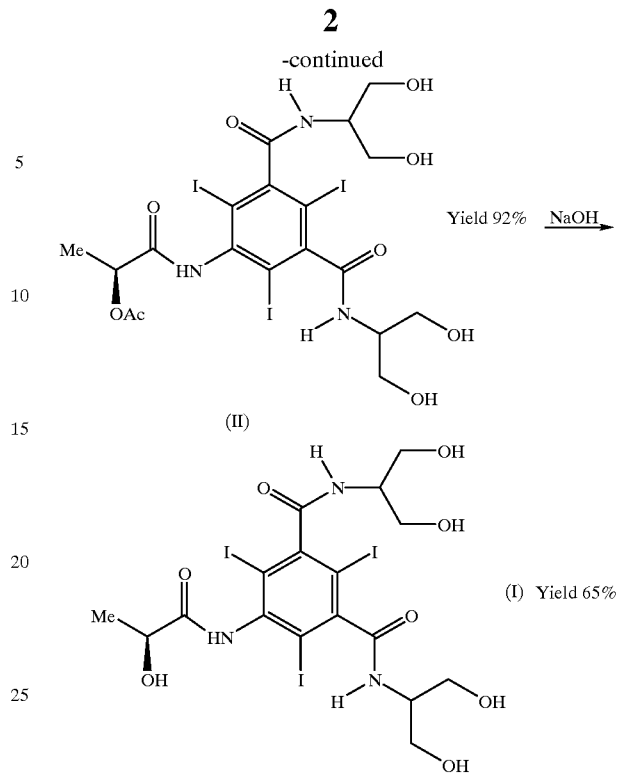

and precisely the reaction of S-(−)-5-[[2-(acetyloxy)-1-oxopropyl]amino]-2,4,6-triiodo-1,3-benzenedicarboxylic acid dichloride of formula (III) dissolved in dimethylacetamide (DMAC) with a slight excess of 2-amino-1,3-propanediol (commonly named serinol) also dissolved in dimethylacetamide, in the presence of tributylamine to give the compound (II), S-N,N'-bis[2-hydroxy-1-(hydroxymethyl)ethyl]-5-[(2-(acetyloxy)-1-oxopropyl)amino]-2,4,6-triiodo-1,3-benzenedicarboxamide.

The ratio between compound (II), serinol and tributylamine, expressed in equivalents, is 1:2.5:2. The reaction is carried out at 50° C. and, after some hours, the desired product is obtained in a 92% yield.

The work up of the reaction mixture, described in the cited Patent, comprises evaporating dimethylacetamide, suspending the oily residue in methylene chloride, taking up repeatedly the precipitate with hot methylene chloride.

The resulting residue is then hydrolysed to Iopamidol with NaOH and the resulting solution is subsequently purified from the salts by treatment with a cationic resin and an anionic one, then recrystallized from ethyl alcohol.

The main problems with this process are the following ones:

the distillation of the solvent under vacuum at the end of the reaction is a very troublesome operation from the industrial point of view, DMAC being a high boiling product (165° C.);

the use of DMAC gives rise to the presence of N-[2-hydroxy-1-(hydroxymethyl)ethyl]-N'-dimethyl-5-[(2-hydroxy-oxopropyl)amino]-2,4,6-triiodo-1,3-benzenedicarboxamide

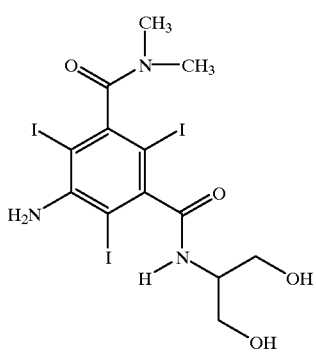

impurity I 10 i.e. one of the seven impurities of Iopamidol described in Pharmeuropa, vol. 6, n°4, Dececember 1994, p. 343–345, which is essentially ascribable to the production of dimethylamine by DMAC during the work up of the reaction;

furthermore, the use of such a high boiling solvent is troublesome and difficult as traces thereof remain in the recovered solid product, which traces must not, however, exceed 650 ppm (USP limit for Iopamidol).

A first attempt to replace DMAC consists in GB Patent 2,272,218 (priority Oct. 27, 1992), which only discloses the preparation of compound (II) by using solvents different from DMAC, i.e. acetone or lower alcohols ($C_1$–$C_4$), in the presence of a base, preferably tributylamine.

As recognized by the inventors themselves in GB patent application 2.311.524, which has been published subsequently and will be discussed in the following, Iopamidol obtained from intermediate (II), albeit having an acceptable purity level, also contained different impurities instead of impurity I.

The medical profession and the rules concerning the marketing authorizations of medicaments, require medicaments with extremely low impurities contents so as to minimize the related risks of side-effects or toxic effects for the patient.

In the case of the iodinated contrast agents such need is particularly justified as the total amount of product administered is many orders of magnitude higher than other medicaments. Only by way of example, the dose or opacifying agent injected can reach and even exceed 150 g.

In fact, the pharmacopoeia standards of Iopamidol have recently been modified, (Italian Pharmacopoeia IX, 3rd revision, 1994; US Pharmacopoeia XXIII, 5th revision, Nov. 15, 1996) in that Iopamidol should contain a maximum of 0.25% impurities.

Recently published GB patent application 2,311,524 (priority Mar. 29, 1996), discloses an alternative method for the preparation of Iopamidol with such purity characteristics.

GB 2,311,524 discloses the preparation of compound (I), using N-methylpyrrolidone as reaction solvent, in the presence of a base, preferably selected from serinol, tributylamine, triethylamine or an inorganic carbonate, and it claims a higher purity of the resulting compound (II) which favourably affects the final purity of Iopamidol.

The preferred process described comprises the reaction of compound (III) with serinol in N-methylpyrrolidone and in the presence of previously purified triethylamine or sodium carbonate. The subsequent treatment of the resulting crude through a battery of ion exchange resins (strongly cationic, weakly anionic, strongly anionic, weak anionic, as described in GB 2.287.024) gives the final compound Iopamidol, with a purity which apparently meets the pharmacopoeia standards.

It is therefore evident from the prior art the increasing need to avoid the use of DMAC, which would also be advantageous in terms of impurities present in Iopamidol while improving the carrying out of the industrial process.

Moreover, N-methylpyrrolidone belongs to the same class of dipolar aprotic solvents as DMAC and it has the same boiling point characteristics, and it is therefore difficult to be removed completely.

It has now surprisingly been found that Iopamidol can be prepared in accordance with the pharmacopoeia standards by the process of the invention comprising:
a novel method for the preparation of compound (II);
the easy transformation of the resulting compound (II) into Iopamidol, involving neither basic hydrolysis nor complex chromatographic treatments.

It is therefore the object of the present invention a process for the preparation of compound (I) comprising the formation of compound (II) by reaction of compound (III) in the presence of only serinol, without solvent, followed by hydrolysis of the acetate group.

It has surprisingly been found that the reaction can be carried out without solvent and without addition of a base, in particular tributylamine as in the prior art, thereby effectively solving the problems mentioned above connected with the presence of DMAC, while obtaining a final product with the purity characteristics in accordance with the pharmacopoeia standards.

As already described in international patent application WO 92/14539, it was already known from the prior art that the reaction can be carried out without a base, using more than 4 equivalents of serinol, which acts as binding agent of the hydrochloric acid formed during the reaction. The reaction was however carried out still in DMAC thus involving the above mentioned problems.

It has surprisingly been found that adding serinol in a molar ratio to compound (III) ranging from 6 to 25, preferably from 8 to 16, the use of a solvent to carry out the condensation reaction between compound (III) and serinol is no more necessary.

Moreover, the serinol excess allows to avoid the addition of a base for the subsequent hydrolysis of compound (II) to Iopamidol.

The temperature of the condensation reaction can range from 30° C. to 70° C., preferably from 38 to 55° C.

The time of the condensation reaction can range from 24 to 100 h, preferably from 40 to 72 h.

At the end of the reaction between serinol and compound (III), monitored by HPLC analysis, the acetate group is hydrolysed by addition of water, preferably in amounts of 2 to 4 kg of water per mol of compound (III): the solution is already basic due to the presence of the serinol excess.

The temperature of the solution is suitably adjusted to 50–70° C., preferably 55–65° C., and kept for a time ranging from 1 to 8 h, preferably from 2 to 5 h. At the end the mixture is neutralized by addition of HCl.

Operating according to the process of the invention, the final reaction mixture containing compound (I), only contains: serinol, serinol hydrochloride, serinol acetate. The only cation present is therefore only serinol thus involving an improvement in the Iopamidol desalting and purification processes.

The absence of dipolar aprotic solvents in the final solution, which are conversely always present in the prior art, allows to purify compound (I) without use of rather expensive industrial apparatuses, such as the nanofiltration apparatus for the preliminary desalting (see WO 92/14539) and the removal of DMAC or the battery of columns first mentioned when using N-methylpyrrolidone (see GB 2,311, 524).

The process of the present invention comprises a chromatographic purification on a conventional column comprising a solid phase selected from the group consisting of highly cross-linked macroporous styrene resins, preferably Amberlite® XAD 1600, 1600 T and 16 (Rohm & Haas) or equivalents thereof commercialized by other producers. The elution is carried out with water, washing until disappearance of the compound, monitored by UV analysis.

After concentrating the aqueous phase, desalting is carried out by a battery (arranged in series or in mixed bed) of a sulfonic strongly cationic resin, regenerated in the acidic form, and a secondary amine medium anionic resin, regenerated in OH⁻ form.

The preferred cationic resins are selected from the group consisting of: Dowex C 350, Amberjet 1200, Amberlite IR 120.

The preferred anionic resin is Relite MG 1.

The desalted solution is concentrated and purified by crystallization from a suitable solvent, as already known in literature (GB 1,472,050, GB 2,708,601, U.S. Pat. No. 5,689,002, WO 97/02235, EP 747344).

Iopamidol obtained by the process of the invention has an impurities content not higher than 0.18% by HPLC analysis, as described in Pharmacopoeia (see above). Neither DMAC from any previous steps for the preparation of compound (III), nor other solvents are found in amounts higher than the requirements of ICH (International Conference on Harmonization) for the presence of residual solvents in pharmaceuticals.

The absence of DMAC or other dipolar aprotic solvents allows to reduce the amount of the crystallization solvent to about one third compared with the prior art, in that the solvent entrainment effect by the dipolar aprotic solvent is no longer present.

Moreover the use of serinol as the base, besides removing the impurity I, reduces the risk of formation of S-N,N'-bis [2-hydroxy-1-(hydroxymethyl)ethyl]-5-amino-2,4,6-triiodo-1,3-benzenedicarboxamide of formula (IV)

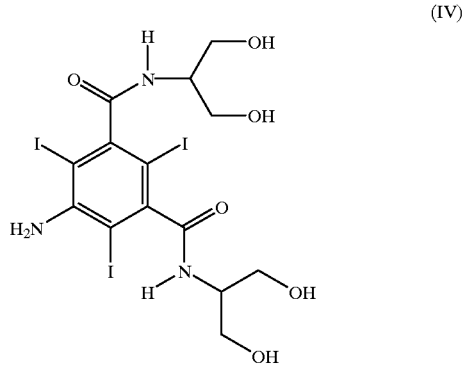

(IV)

in which a free amino group is present, and that therefore belongs to the harmful class of aromatic amines, which is very difficult to remove from compound (I) once formed. The decrease in this by-product in the process of the present invention, is likely due to the lower basicity of serinol in the complementary hydrolysis reaction of the amide having lactic acid at the 5-position.

The following examples illustrate the best experimental conditions to carry out the process of the invention.

EXPERIMENTAL SECTION

Example 1

Preparation of Iopamidol using an 8,3 molar excess to compound (III), without solvents.

127.5 g (0.179 mol) of compound (III) (prepared as described in U.S. Pat. No. 5,672,735) are placed in a 1 L flask and added with 136 g (1.49 mol) of serinol.

The flask is connected with a rotary evaporator, equipped with water bath thermostatized at a temperature of 48° C. and kept under nitrogen atmosphere. Rotation is continued at constant temperature for 58 hours. After said time, 400 g of water are added, heating at 52° C. for 4 hours to complete saponification. The mixture is neutralized with 34% HCl and the aqueous solution is eluted on XAD 1600 (500 mL) with water until disappearance of the product.

The eluate is concentrated to a volume of about 1 L and the solution is then eluted on a cationic resin (Dowex C350, 1.2 L regenerated in H⁺ form) and on an anionic resin (Relite MG 1, 1.0 L, regenerated in OH³¹ form) . Afterwards water is concentrated under vacuum and the residue is crystallized from sec-butanol, to obtain 108 g (0.14 mol) of the desired product.

Yield: 78%

HPLC assay: 99.80% (Area %)

HPLC method: see US Pharmacopoeia XXIII, 5th revision, Nov. 15, 1996

Recovery of Serinol

After eluting the solution of the product on the resin (Dowex C350, 1.2 L regenerated in H⁺ form) serinol is displaced with 750 g of a 4% by weight ammonia solution, then washed with deionized water to neutral pH.

The resulting solution is concentrated under 12 mmHg at a temperature of 50–60° C. to remove ammonia, obtaining a residue containing about 5–10% of residual water. 250 g of anhydrous 2-butanol are added and the mixture is cooled to 5° C. for 3 hours, then filtered and dried at 30° C. under nitrogen stream to obtain 85 g of serinol of good quality which can be recycled in the synthesis of Iopamidol.

Example 2

Preparation of Iopamidol using a 12 molar excess to compound (III), without solvents 127.5 g (0.179 mol) of compound (III) (prepared as described in U.S. Pat. No. 5,672,735) are placed in a 1 L flask and added with 196 g (2.15 mol) of serinol. The flask is connected with a rotary evaporator, equipped with water bath thermostatized at a temperature of 44° C. and kept under nitrogen atmosphere. Rotation is continued at constant temperature for 70 hours. After that, 400 g of water are added, heating at 55° C. for 2 hours to complete saponification. The mixture is neutralized with 34% HCl and the aqueous solution is eluted on XAD 1600 (500 mL) with water until disappearance of the product.

The eluate is concentrated to a volume of about 1 L and the solution is then eluted on a cationic resin (Dowex C350, 1.9 L regenerated in H⁺ form) and on an anionic resin (Relite MG 1, 1.5 L, regenerated in OH⁻ form).

Afterwards water is removed under vacuum and the residue is crystallized from sec-butanol, to obtain 118 g (0.15 mol) of the desired product.

Yield: 84%

HPLC assay: 99.82% (Area %)

HPLC method: see US Pharmacopoeia XXIII, 5th revision, Nov. 15, 1996.

Recovery of Serinol

After eluting the solution of the product on the resin (Dowex C350, 1.9 L regenerated in H⁺ form) serinol is displaced with 1200 g of a 4% by weight ammonia solution, then washed with deionized water to neutral pH.

The resulting solution is concentrated under 12 mmHg at a temperature of 50–60° C. to remove ammonia, obtaining a residue containing about 5–10% of residual water. 380 g of anhydrous 2-butanol are added and the mixture is cooled to 5° C. for 3 hours, then filtered and dried at 30° C. under nitrogen stream to obtain 125 g of serinol of good quality which can be recycled in the synthesis of Iopamidol.

Example 3

Preparation of Iopamidol using a 16 molar excess to compound (III), without solvents 127.5 g (0.179 mol) of compound (III) (prepared as described in U.S. Pat. No. 5,672,735) are placed in a 1 L flask and added with 261 g (2.87 mol) of serinol. The flask is connected with a rotary evaporator, equipped with water bath thermostatized at a temperature of 48° C. and kept under nitrogen atmosphere. Rotation is continued at constant temperature for 48 hours. After that, 400 g of water are added, heating at 57° C. for 2 hours to complete saponification. The mixture is neutralized with 34% HCl and the aqueous solution is eluted on XAD 1600 (500 mL) with water until disappearance of the product.

The eluate is concentrated to a volume of about 1 L and the solution is then eluted on a cationic resin (Dowex C350, 2.4 L regenerated in H⁺ form) and on an anionic resin (Relite MG 1, 1.0 L, regenerated in OH⁻ form). Afterwards water is removed under vacuum and the residue is crystallized from sec-butanol, to obtain 124 g (0.16 mol) of the desired product.

Yield: 90%

HPLC assay: 99.86% (Area %)

HPLC method: see US Pharmacopoeia XXIII, 5th revision, Nov. 15, 1996.

Recovery of Serinol

After eluting the solution of the product on the resin (Dowex C350, 1.2 L regenerated in H³⁰ form) serinol is displaced with 1650 g of a 4% by weight ammonia solution, then washed with deionized water to neutral pH.

The resulting solution is concentrated under 12 mmHg at a temperature of 50–60° C. to remove ammonia, obtaining a residue containing about 5–10% of residual water. 500 g of anhydrous 2-butanol are added and the mixture is cooled to 5° C. for 3 hours, then filtered and dried at 30° C. under nitrogen stream to obtain 195 g of serinol of good quality which can be recycled in the synthesis of Iopamidol.

Example 4

Preparation of Iopamidol using a 12 molar excess to compound (III), without solvents 1.27 kg (1.79 mols) of compound (III) (prepared as described in U.S. Pat. No. 5,672,735) are placed in a 5 L reactor with water jacket and fitted with an "impeller" mechanical stirrer and thermo-stat; and 1.96 kg (21.5 mols) of serinol are added thereto.

The reactor is blanketed with nitrogen, keeping said atmosphere during the whole reaction. Thermo-stat is set at 45° C. and said temperature is kept for 70 hours, slowly stirring at 5–10 rpm. During the reaction, the solid turns to a melt mass which becomes increasingly more fluid. After that, 0.4 kg of water pre-heated at 55° C. are loaded, keeping said temperature for two hours to complete saponification.

The mixture is neutralized with 34% HCl (w/w) to pH 6.5–7.5 and the aqueous solution is eluted on a XAD 1600 resin (500 mL) washing with water to a Iopamidol residual concentration below 0.05%. The eluate is concentrated to about 6 L and the solution is eluted on a cationic resin (Dowex C350 or similar regenerated in H⁺ form, volume 1.9 L) and subsequently on an anionic resin (Relite MG1 or similar, regenerated in OH⁻ form, volume 1.5 L). The solution is concentrated under vacuum (12 mbars, 50° C.) and the residue is crystallized from sec-butanol, to obtain 1.2 kg of Iopamidol.

Yield 84.9%

HPLC assay: 99.80%

HPLC method: see US Pharmacopoeia XXIII, 5th revision, Nov. 15, 1996.

Recovery of Serinol

Serinol is recovered according to the procedure described in example 2, adjusting the amount of resin, regenerant and washing water, and of crystallization solvent.

What is claimed is:

1. A process for the preparation of S-N,N'-bis[2-hydroxy-1-(hydroxymethyl)ethyl]-5-[(2-hydroxy-1-oxo-propyl)amino]-2,4,6-triiodo-1,3-benzenedicarboxamide comprising the reaction of S-(−)-5-[[2-(acetyloxy)-1-oxopropyl]amino]-2,4,6-triiodo-1,3-benzenedicarboxylic acid dichloride (III) with 2-amino-1,3-propanediol (serinol) without a solvent followed by hydrolysis of the acetate group.

2. A process as claimed in claim 1, in which the minimum molar ratio between 2-amino-1,3-propanediol and S-(−)-5-[[2-(acetyloxy)-1-oxopropyl]amino]-2,4,6-triiodo-1,3-benzendicarboxylic acid dichloride ranges from 6 to 25.

3. A process as claimed in claim 2, in which the minimum molar ratio between 2-amino-1,3-propanediol and S-(−)-5-[[2-(acetyloxy)-1-oxopropyl]amino]-2,4,6-triiodo-1,3-benzendicarboxylic acid dichloride ranges from 8 to 16.

4. A process according to claim 1 which the reaction temperature ranges from 38 to 85° C. and the reaction time ranges from 40 to 72 hours.

5. A process according to claim 1, which at the end of the reaction between serinol and compound (III) the acetate group is hydrolysed by addition of water, heating the solution to 50–70° C., keeping said temperature for a time ranging from 1 to 8 h; the solution is neutralized by addition of HCl, concentrated, and purified by elution on a highly cross-linked styrene macroporous resin and subsequently on a sulfonic strongly cationic resin, regenerated in the acidic form, and a medium secondary amine anionic resin, regenerated in OH⁻ form.

6. A process as claimed in claim 5, in which the temperature of the hydrolysis reaction of the acetate group ranges from 55 to 65° C. and the duration of said reaction ranges from 2 to 5 h.

7. A process according to claim 5, in which the styrene resins are selected from the group consisting of: Amberlite ⁽ᴿ⁾ XAD 1600, 1600 T and 16; the cationic resins are selected from the group consisting of: Dowex C 350, Amberjet 1200, Amberlite IR 120; the anionic resin is Relite MG 1.

* * * * *